United States Patent
Fung et al.

(10) Patent No.: US 10,369,247 B2
(45) Date of Patent: Aug. 6, 2019

(54) ADHESIVE ARTICLE AND METHOD OF MAKING THE SAME

(71) Applicant: 3M INNOVATIVE PROPERTIES COMPANY, St. Paul, MN (US)

(72) Inventors: Simon S. Fung, Woodbury, MN (US); Michael D. Determan, Mahtomedi, MN (US); Kiu-Yuen Tse, Woodbury, MN (US); David T. Amos, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/367,476

(22) PCT Filed: Dec. 20, 2012

(86) PCT No.: PCT/US2012/070772
§ 371 (c)(1),
(2) Date: Jun. 20, 2014

(87) PCT Pub. No.: WO2013/096535
PCT Pub. Date: Jun. 27, 2013

(65) Prior Publication Data
US 2014/0349108 A1   Nov. 27, 2014

Related U.S. Application Data

(60) Provisional application No. 61/579,064, filed on Dec. 22, 2011.

(51) Int. Cl.
*C08K 5/56* (2006.01)
*C09J 7/25* (2018.01)
(Continued)

(52) U.S. Cl.
CPC ............ *A61L 15/58* (2013.01); *A61L 15/225* (2013.01); *A61L 15/26* (2013.01);
(Continued)

(58) Field of Classification Search
CPC .......... C08L 71/02; C08L 67/00; C09J 183/04
See application file for complete search history.

(56) References Cited

U.S. PATENT DOCUMENTS

| 2,676,182 A | 4/1954 | Daudt |
| 2,736,721 A | 2/1956 | Dexter |

(Continued)

FOREIGN PATENT DOCUMENTS

| JP | H02-36234 | 2/1990 |
| JP | 07227947 A * | 8/1995 |

(Continued)

OTHER PUBLICATIONS

Derwent Abstract of JP 2001-179912. See above for date and inventor.*

(Continued)

*Primary Examiner* — Victor S Chang (57) ABSTRACT

Adhesive articles that include a substrate and a silicone adhesive are disclosed. The articles also include a polymer containing poly(propylene oxide) units and optionally poly (ethylene oxide) units and having a number average molecular weight of at least 1000 grams per mole. The polymer may either be incorporated into the substrate or may be used as a primer on the substrate. If the polymer includes poly (ethylene oxide) units, the copolymer typically has a weight ratio of poly(ethylene oxide) to poly(propylene oxide) of up to 3:1, or if the copolymer has a number average molecular weight of at least 10,000 grams per mole, the weight ratio of poly(ethylene oxide) to poly(propylene oxide) is up to 2:1. Methods of making the adhesive articles are also disclosed.

20 Claims, 1 Drawing Sheet

(51) Int. Cl.

| | | |
|---|---|---|
| *C09J 7/50* | (2018.01) | |
| *A61L 15/22* | (2006.01) | |
| *A61L 15/26* | (2006.01) | |
| *A61L 15/58* | (2006.01) | |
| *C08G 18/10* | (2006.01) | |
| *C08G 18/28* | (2006.01) | |
| *C08G 18/48* | (2006.01) | |
| *C08G 18/75* | (2006.01) | |
| *C08G 77/12* | (2006.01) | |
| *C08G 77/20* | (2006.01) | |
| *C08L 67/00* | (2006.01) | |
| *C08L 71/02* | (2006.01) | |
| *C08L 75/04* | (2006.01) | |
| *C08L 83/00* | (2006.01) | |
| *C08L 83/04* | (2006.01) | |
| *C09J 183/04* | (2006.01) | |

(52) U.S. Cl.
CPC ....... *C08G 18/4837* (2013.01); *C08G 18/758* (2013.01); *C08K 5/56* (2013.01); *C08L 71/02* (2013.01); *C08L 83/00* (2013.01); *C09J 7/25* (2018.01); *C09J 7/50* (2018.01); *C09J 183/04* (2013.01); *C08G 77/12* (2013.01); *C08G 77/20* (2013.01); *C09J 2467/006* (2013.01); *C09J 2471/003* (2013.01); *C09J 2471/006* (2013.01); *C09J 2475/006* (2013.01); *C09J 2483/00* (2013.01); *Y10T 428/2809* (2015.01); *Y10T 428/2843* (2015.01); *Y10T 428/2852* (2015.01)

(56) References Cited

U.S. PATENT DOCUMENTS

| | | | |
|---|---|---|---|
| 3,627,851 | A | 12/1971 | Brady |
| 3,772,247 | A | 11/1973 | Flannigan |
| 4,935,484 | A | 6/1990 | Wolfgruber |
| 5,082,706 | A | 1/1992 | Tangney |
| 5,110,890 | A | 5/1992 | Butler |
| 5,248,739 | A | 9/1993 | Schmidt |
| 5,302,685 | A | 4/1994 | Tsumura |
| 5,319,040 | A | 6/1994 | Wengrovius |
| 5,891,530 | A | 4/1999 | Wright |
| 6,129,971 | A | 10/2000 | Brandt |
| 6,500,526 | B1 | 12/2002 | Hannington |
| 7,371,464 | B2 | 5/2008 | Sherman |
| 7,915,370 | B2 | 3/2011 | Sherman |
| 8,557,378 | B2 | 10/2013 | Yamanaka |
| 2003/0104224 | A1 | 6/2003 | Kuroda |
| 2003/0165676 | A1 | 9/2003 | Zhou |
| 2004/0185258 | A1 | 9/2004 | Fukushi |
| 2007/0077348 | A1* | 4/2007 | Lu .......... A61K 38/10 427/2.26 |
| 2007/0100306 | A1 | 5/2007 | DiZio et al. |
| 2008/0187750 | A1 | 8/2008 | Sherman |
| 2009/0229732 | A1 | 9/2009 | Determan |
| 2011/0212325 | A1* | 9/2011 | Determan .......... A61L 15/58 428/332 |

FOREIGN PATENT DOCUMENTS

| | | |
|---|---|---|
| JP | 2001179912 A * | 7/2001 |
| JP | 2008-143923 | 6/2008 |
| JP | 2010-184953 | 8/2010 |
| WO | WO 2005-102403 | 11/2005 |
| WO | WO 2009-114683 | 9/2009 |
| WO | WO 2010-056543 | 5/2010 |
| WO | WO 2010-056544 | 5/2010 |
| WO | WO 2010-080567 | 7/2010 |
| WO | WO 2011-068754 | 6/2011 |
| WO | WO 2013-025955 | 2/2013 |
| WO | WO 2013-096530 | 6/2013 |

OTHER PUBLICATIONS

Abstract of JP 7-227947. See above for date and inventor.*
Translation of JP 2001-179912, see PTO-892 mailed Jan. 29, 2016 for date and inventor.*
Translation of JP 07227947, see PTO-892 mailed Jan. 29, 2016 for date and inventor.*
Mark, "Encyclopedia of Polymer Science and Engineering", vol. 15, 1989, pp. 265-270.
International Search Report for PCT International Application No. PCT/US2012/070772, dated May 24, 2013, 3pgs.
The People's Republic of China Search Report, Application No. 201280063881.0, dated Apr. 23, 2015.

* cited by examiner

ADHESIVE ARTICLE AND METHOD OF MAKING THE SAME

CROSS REFERENCE TO RELATED APPLICATIONS

This application is a national stage filing under 35 U.S.C. 371 of PCT/US2012/070772, filed Dec. 20, 2012, which claims priority to U.S. Application No. 61/579,064, filed Dec. 22, 2011, the disclosure of which is incorporated by reference in its entirety herein.

BACKGROUND

Silicone adhesives, including silicone pressure sensitive adhesives, may have a variety of desirable properties. In a variety of applications silicone adhesives may exhibit, for example, good adhesion over a wide temperature range, resistance to environmental factors such as oxidation and ultraviolet light, high moisture vapor transmission rates, and good electrical properties. Certain silicone adhesives are useful for medical tapes and dressings because the silicone adhesive can provide adhesion while gently removing from the skin without causing trauma or stripping skin cells or hair. Some of these silicone adhesives are described in U.S. Pat. App. Pub. No. 2011/0212325 (Determan et al.) and Int. Pat. App. Pub. No. WO 2005/102403 (Gantner et al.).

In certain silicone adhesive tapes, delamination of the silicone adhesive from the tape backing can be a problem. Such delamination can make it difficult to remove the adhesive from skin, for example, and limits the ability to reuse the tape.

SUMMARY

The present disclosure provides adhesive articles that include a silicone adhesive disposed on a thermoplastic polyurethane or polyester substrate. The adhesive articles include poly(propylene oxide) or copolymers of poly(ethylene oxide) and poly(propylene oxide) either blended into the substrate or used as a primer on the substrate. The primers can may also include polyurethanes or polyesters with poly(propylene oxide) or copolymerized poly(ethylene oxide) and poly(propylene oxide) segments. Adhesive articles disclosed herein typically have better adhesion between the radiation cross-linked silicone adhesive and the substrate than comparative adhesive articles that do not include the poly(propylene oxide) polymers or copolymers. The adhesion is improved even though the poly(propylene oxide) polymers or copolymers do not contain reactive functional groups that can bond with the substrate and/or the silicone adhesive.

In one aspect, the present disclosure provides an adhesive article that includes a substrate comprising a polymer blend and a silicone adhesive disposed on the substrate. The polymer blend includes at least one of a thermoplastic polyurethane or a thermoplastic polyester and polymer having a number average molecular weight of at least 1000 grams per mole. The polymer is a poly(propylene oxide) or a copolymer of poly(ethylene oxide) and poly(propylene oxide). The copolymer has a weight ratio of poly(ethylene oxide) to poly(propylene oxide) of up to 3:1, with the provision that if the copolymer has a number average molecular weight of at least 10,000 grams per mole, the weight ratio of poly(ethylene oxide) to poly(propylene oxide) is up to 2:1.

In another aspect, the present disclosure provides a method of making such an adhesive article. The method includes providing the substrate, coating a silicone adhesive composition onto the substrate, and crosslinking the silicone adhesive composition to form the silicone adhesive. In some embodiments, crosslinking comprises exposing the silicon adhesive composition to radiation to form a radiation cross-linked silicone adhesive. In some of these embodiments, radiation includes at least one of electron-beam or gamma radiation.

In another aspect, the present disclosure provides method of improving adhesion of a silicone adhesive to a substrate comprising a thermoplastic polyurethane or thermoplastic polyester. The method includes blending a polymer with the thermoplastic polyurethane or thermoplastic polyester to form the substrate. The polymer has a number average molecular weight of at least 1000 grams per mole and is a poly(propylene oxide) or a copolymer of poly(ethylene oxide) and poly(propylene oxide) having a weight ratio of poly(ethylene oxide) to poly(propylene oxide) of up to 3:1, with the provision that if the copolymer has a number average molecular weight of at least 10,000 grams per mole, the weight ratio of poly(ethylene oxide) to poly(propylene oxide) is up to 2:1.

In another aspect, the present disclosure provides an adhesive article that includes a substrate comprising at least one of a thermoplastic polyurethane or a thermoplastic polyester, a primer layer disposed on the substrate, and a silicone adhesive disposed on the primer layer. The primer layer includes a polymer, wherein the polymer is a poly(propylene oxide) having a number average molecular weight of at least 1000 grams per mole, a copolymer of poly(ethylene oxide) and poly(propylene oxide) having a number average molecular weight of at least 1000 grams per mole, or a thermoplastic polymer comprising poly(propylene oxide) segments or copolymerized poly(ethylene oxide) and poly(propylene oxide) segments. In the copolymer of poly(ethylene oxide) and poly(propylene oxide), the weight ratio of poly(ethylene oxide) to poly(propylene oxide) is up to 3:1, with the provision that if the copolymer has a number average molecular weight of at least 10,000 grams per mole, the weight ratio of poly(ethylene oxide) to poly(propylene oxide) is up to 2:1. In some embodiments, the thermoplastic polymer in the primer layer is a thermoplastic polyurethane or thermoplastic polyester comprising the poly(propylene oxide) segments or a thermoplastic polyurethane or thermoplastic polyester comprising the segments of copolymerized poly(ethylene oxide) and poly(propylene oxide).

In another aspect, the present disclosure provides a method of making such an adhesive article. The method includes coating the primer layer onto the substrate, coating a silicone adhesive composition onto the primer layer, and crosslinking the silicone adhesive composition to form the silicone adhesive. The primer layer typically improves the adhesion between the substrate and the silicone adhesive. In some embodiments, crosslinking comprises exposing the silicon adhesive composition to radiation to form a radiation crosslinked silicone adhesive. In some of these embodiments, radiation includes at least one of electron-beam or gamma radiation.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

"Alkyl" and the prefix "alk-" are inclusive of both straight chain and branched chain alkyl groups. Alkyl groups can have up to 30 carbons (in some embodiments, up to 20, 15, 12, 10, 8, 7, 6, or 5 carbons) unless otherwise specified.

"Cycloalkyl" includes monocyclic or polycyclic groups having from 3 to 10 (in some embodiments, 3 to 6 or 5 to 6) ring carbon atoms.

"Alkylene" refers to a multivalent (e.g., divalent) form of the "alkyl" groups defined above.

"Arylalkylene" refers to an "alkylene" moiety to which an aryl group is attached.

The term "aryl" as used herein includes carbocyclic aromatic rings or ring systems, for example, having 1, 2, or 3 rings and optionally containing at least one heteroatom (e.g., O, S, or N) in the ring. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

The term "polyurethane" as used herein includes compounds having more than one carbamate and/or urea group and can also contain biuret, allophanate, uretdione, or isocyanurate linkages in any combination.

Number average molecular weights can be measured, for example, by gel permeation chromatography (i.e., size exclusion chromatography) or by nuclear magnetic resonance spectroscopy using techniques known in the art.

The term "pressure sensitive adhesive" as used herein refer to adhesives that possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as PSAs are polymers designed and formulated to exhibit the requisite viscoelastic properties resulting in a desired balance of tack, peel adhesion, and shear holding power.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

While the above-identified drawings and figures set forth embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of this invention. The figures may not be drawn to scale.

DETAILED DESCRIPTION

Figure 1:
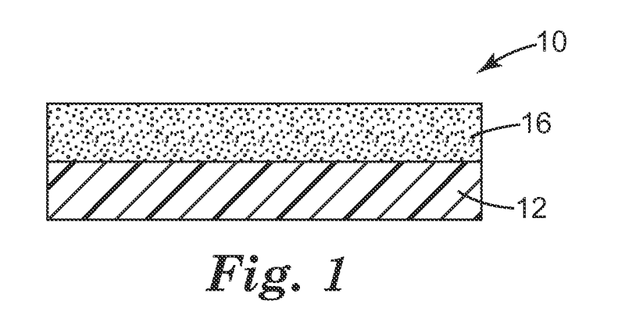
FIG. 1 is a schematic side view of an embodiment of an adhesive article according to the present disclosure.
Figure 2:
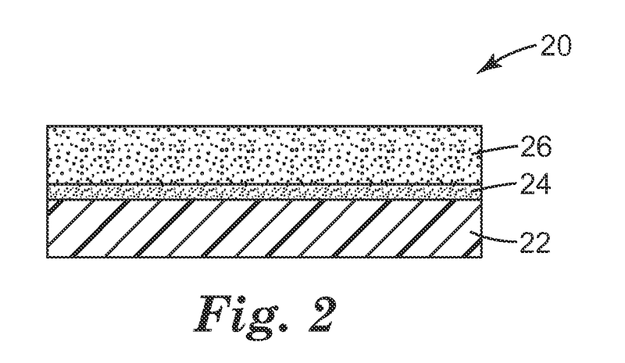
FIG. 2 is a schematic side view of another embodiment of an adhesive article according to the present disclosure.

FIG. 1 is a schematic side view of an embodiment of an article 10 with a silicone adhesive 16 applied to a substrate 12. FIG. 2 is a schematic side view of another embodiment of an adhesive article 20. In adhesive article 20, primer layer 24 is disposed on substrate 22. Silicone adhesive 26 is disposed on the primer layer.

Substrates 12, 22 included in the adhesive articles according to and/or made according to the present disclosure include a thermoplastic polyurethane, a thermoplastic polyester, or a combination thereof. The thermoplastic polyurethane or thermoplastic polyester may be selected to have a high moisture vapor rate. Such substrates are useful, for example, in wound dressings and bandages. In some embodiments, the substrate includes a thermoplastic polyurethane. A variety of thermoplastic polyurethanes may be useful, including polyether-based polyurethanes and polyester-based polyurethanes. For example, a polyether or polyester with isocyanate-reactive terminal groups may be reacted with an aromatic, aliphatic, arylalkylenyl, or cycloaliphatic diisocyanate to provide a useful polyurethane. Exemplary suitable polyurethanes include those commercially available, for example, from Lubrizol, Wickliffe, Ohio, under the trade designation "ESTANE" (e.g., "ESTANE 58237", "ESTANE 58309", or "ESTANE 58213") and from Huntsman, The Woodlands, Tex., under the trade designation "IROGRAN" (e.g., "IROGRAN A 60 E 4902"). A variety of thermoplastic polyesters may also be useful. Exemplary suitable polyesters include those commercially available, for example, from E.I. du Pont de Nemours and Company, Wilmington, Del., under the trade designation "HYTREL".

In some embodiments, including the embodiment illustrated in FIG. 1, the substrate 12 also includes a polymer, which may be a poly(propylene oxide) homopolymer or a copolymer of poly(ethylene oxide) and poly(propylene oxide). In these embodiments, the polymer is physically blended with the thermoplastic polyurethane or thermoplastic polyester. Typically, the polymer is not reacted with the thermoplastic polyurethane or thermoplastic polyester in the substrate. In some embodiments, at least a portion of the polymer is not covalently attached to the thermoplastic polyurethane or thermoplastic polyester in the substrate.

The polymer included in the substrate 12 has a number average molecular weight of at least 1000 grams per mole. In some embodiments, the polymer has a number average molecular weight of at least 1500 or 2000 grams per mole. The polymer typically has a number average molecular weight of up to 20,000 grams per mole, in some embodiments, up to 15,000 grams per mole. For example, the polymer may have a number average molecular weight in a range from 1000 to 20,000 grams per mole, 1000 to 15,000 grams per mole, or 2000 to 13000 grams per mole. The number average molecular weight of at least 1000 grams per mole allows the polymer to be useful as a film-forming polymer and compatible with the substrate thermoplastic.

When the polymer is a copolymer of poly(ethylene oxide) and poly(propylene oxide), the copolymer may be a block copolymer, a gradient copolymer, or a random copolymer. Exemplary useful poly(ethylene oxide) and poly(propylene oxide) block copolymers include triblock copolymers with the general formula RO—$(CH_2CH_2O)_n$—$(CH(CH_3)CH_2O)_m$—$(CH_2CH_2O)_n$—R or RO—$(CH(CH_3)CH_2O)_m$—

$(CH_2CH_2O)_p$—$(CH(CH_3)CH_2O)_m$—R, wherein each n is independently from 1 to about 40 (in some embodiments, 1 to 40, 5 to 39, 10 to 35, or 10 to 30); p is in a range from 10 to about 80 (in some embodiments, 10 to 80, 10 to 79, 15 to 75, or 15 to 70); each m is independently in a range from 1 to about 80 (in some embodiments, 1 to 75, 1 to 70, 1 to 65, or 1 to 60), and each R is independently hydrogen, a $C_1$ to $C_4$ alkyl group, or an aryl group. In some embodiments, each R is hydrogen. Several triblock polymers of poly (ethylene oxide) and poly(propylene oxide) are commercially available, for example, from BASF, Florham Park, N.J., under the trade designation "PLURONIC™".

Random copolymers of poly(ethylene oxide) and poly (propylene oxide) are also useful and are available from a variety of commercial sources (e.g., Sigma-Aldrich, St. Louis, Mo.). These random copolymers may also be terminated with hydroxyl groups, alkoxy groups, aryloxy groups, or a combination thereof.

When the polymer useful for practicing the present disclosure is a copolymer of poly(ethylene oxide) to poly (propylene oxide) (e.g., a random copolymer or a block copolymer), the copolymer typically has a weight ratio of poly(ethylene oxide) to poly(propylene oxide) of up to 3:1. In some embodiments, including embodiments wherein the copolymer has a number average molecular weight of at least 10,000 grams per mole, the weight ratio of poly (ethylene oxide) to poly(propylene oxide) is up to 2:1. In some embodiments, the weight ratio of poly(ethylene oxide) to poly(propylene oxide) is up to 1:1, and in some embodiments, the weight percent of poly(propylene oxide) in the copolymer exceeds the weight percent of poly(ethylene oxide). When the weight ratio of poly(ethylene oxide) to poly(propylene oxide) exceeds 3:1, or 2:1 at molecular weights of higher than 10,000 grams per mole, the crystallinity in the copolymer may become too high. In these instances, the substrate may become too stiff, and the adhesion between the substrate and the silicone adhesive may be diminished. However, as shown in the Examples, below, when the weight ratio of poly(ethylene oxide) to poly(propylene oxide) is up to 3:1, or 2:1 at molecular weights of higher than 10,000 grams per mole, good adhesion between the substrate and the silicone adhesive is achieved.

In some embodiments, including the embodiment illustrated in FIG. 1, the polymer blend that comprises the substrate 12 includes the poly(propylene oxide) homopolymer or poly(ethylene oxide)/poly(propylene oxide) co-polymer in any of the embodiments described above includes the polymer or copolymer in an amount of up to 15 percent by weight, based on the total weight of the substrate. In some embodiments, the amount of polymer or copolymer in the polymer blend is up to 12 or 10 percent by weight. In some embodiments, the amount of polymer or copolymer in the polymer blend is greater than 2.5 percent by weight. In some embodiments, the amount of polymer or copolymer in the polymer blend is at least 3, 4, or 5 percent by weight, based on the total weight of the substrate.

The substrate that includes the poly(propylene oxide) homopolymer or poly(ethylene oxide)/poly(propylene oxide) co-polymer and at least one of the thermoplastic polyurethane or the thermoplastic polyester may be prepared in a variety of ways. For example, a mixture of the polymer and the thermoplastic polyurethane or polyester and any other desired components may be solution cast by dissolving the polymer blend in a suitable solvent (e.g., tetrahydrofuran or ethyl acetate), coating the resulting solution onto a film (e.g., a polyester film such as polyethylene terephthalate, a paper film, or a polymer-coated paper film), and drying to remove solvent. The substrate may be removed from the film in some embodiments. Or, in other embodiments, the substrate may remain on the film or a portion of the film. It is also possible that the polymer blend may be cast into a film using a solventless process (e.g., melt casting).

In the embodiment shown in FIG. 2, primer layer 24 is disposed on substrate 22, and adhesive composition 26 is disposed on the primer layer. In some embodiments, the primer layer 24 includes a poly(propylene oxide) homopolymer, a copolymer of poly(ethylene oxide) and poly(propylene oxide), a thermoplastic polyurethane including a poly(propylene oxide) segment or a segment including copolymerized poly(propylene oxide) and poly(ethylene oxide), or a thermoplastic polyester terminated including a poly(propylene oxide) segment or a segment including copolymerized poly(propylene oxide) and poly(ethylene oxide). In the primer layer 24, the poly(propylene oxide) homopolymer or the a copolymer of poly(ethylene oxide) and poly(propylene oxide) has a number average molecular weight of at least 1000 grams per mole and may have any number average molecular weight as in any of the embodiments of poly(propylene oxide) homopolymer or the a copolymer of poly(ethylene oxide) and poly(propylene oxide) described above in connection with the substrate. The copolymer of poly(ethylene oxide) and poly(propylene oxide) may be a random, gradient, or block copolymer having any of the ratios of poly(ethylene oxide) to poly (propylene oxide) or any of the terminal groups described above in connection with the substrate.

In some embodiments, the primer layer 24 contains a thermoplastic polyurethane including a poly(propylene oxide) segment or a segment including copolymerized poly (ethylene oxide and poly(propylene oxide). For example, the thermoplastic polyurethane may be an addition polymer of a difunctional isocyanate and a hydroxyl-terminated poly (propylene oxide) or hydroxyl-terminated copolymer of poly(ethylene oxide) and poly(propylene oxide). The primer layer 24 may also contain, in other embodiments, a thermoplastic polyester including a poly(propylene oxide) segment or a segment including copolymerized poly(ethylene oxide) and poly(propylene oxide). For example, the thermoplastic polyester may be an addition polymer of a difunctional carboxylic acid equivalent and a hydroxyl- or amino-terminated poly(propylene oxide) or a hydroxyl- or amino-terminated copolymer of poly(ethylene oxide) and poly(propylene oxide). Depending on the molar ratio of the segment to the difuncational isocyanate or difunctional carboxylic acid equivalent, there may be multiple segments of poly(propylene oxide) or copolymerized poly(ethylene oxide) and poly (propylene oxide) in the addition polymer. In some embodiments, each segment of poly(propylene oxide) or poly (ethylene oxide)/poly(propylene oxide) has a number average molecular weight of at least 1000 grams per mole. In some embodiments, each segment has a number average molecular weight of at least 1500 or 2000 grams per mole. In some embodiments, each segment typically has a number average molecular weight of up to 20,000 grams per mole, in some embodiments, up to 15,000 grams per mole. For example, each segment may have a number average molecular weight in a range from 1000 to 20,000 grams per mole, 1000 to 15,000 grams per mole, or 2000 to 13000 grams per mole. In any of these embodiments, the thermoplastic polyurethane or polyester that contains such segments may have a number average molecular weight of at least 1,000 grams per mole, in some embodiments, in a range from 5,000 grams per mole to 100,000 grams per mole. In some embodiments, the thermoplastic polyurethane or polyester has a number average molecular weight in a range from 10,000 grams per mole to 100,000 grams per mole, or 15,000 grams per mole to 85,000 grams per mole.

When the segment includes copolymerized poly(ethylene oxide) and poly(propylene oxide), the copolymerized units may be in blocks, in a gradient, or random. Exemplary poly(ethylene oxide) and poly(propylene oxide) block copolymers useful for making the thermoplastic polyurethane or thermoplastic polyester include triblock copolymers with the general formula HO—$(CH_2CH_2O)_n$—$(CH(CH_3)CH_2O)_m$—$(CH_2CH_2O)_n$—H or HO—$(CH(CH_3)CH_2O)_m$—$(CH_2CH_2O)_p$—$(CH(CH_3)CH_2O)_m$—H, wherein each n is independently from 1 to about 40 (in some embodiments, 1 to 40, 5 to 39, 10 to 35, or 10 to 30); p is in a range from 10 to about 80 (in some embodiments, 10 to 80, 10 to 79, 15 to 75, or 15 to 70); and each m is independently in a range from 1 to about 80 (in some embodiments, 1 to 75, 1 to 70, 1 to 65, or 1 to 60).

Difunctional amino-terminated poly(propylene oxide) and poly(ethylene oxide)/poly(propylene oxide) compounds are also useful for making the thermoplastic polyurethane in the primer layer. Several of these diamines are commercially available, for example, from Huntsman Corp., The Woodlands, Tex., under the trade designation "JEFFAMINE".

Exemplary poly(ethylene oxide) and poly(propylene oxide) copolymers (e.g., block, gradient, or random copolymers) useful for making the thermoplastic polyurethane or thermoplastic polyester have a weight ratio of poly(ethylene oxide) to poly(propylene oxide) of up to 3:1. In some embodiments, including embodiments wherein the copolymer has a number average molecular weight of at least 10,000 grams per mole, the weight ratio of poly(ethylene oxide) to poly(propylene oxide) is up to 2:1. In some embodiments, the weight ratio of poly(ethylene oxide) to poly(propylene oxide) is up to 1:1, and in some embodiments, the weight percent of poly(propylene oxide) in the copolymer exceeds the weight percent of poly(ethylene oxide). When the weight ratio of poly(ethylene oxide) to poly(propylene oxide) exceeds 3:1, or 2:1 at molecular weights of higher than 10,000 grams per mole, the crystallinity in the copolymer may become too high. In these instances, the primer layer 24 may become too stiff, and the adhesion between the substrate 22 and the silicone adhesive 26 may be diminished.

In embodiments wherein the thermoplastic polymer in the primer layer 24 is a thermoplastic polyurethane, the thermoplastic polyurethane can be made from a variety of diisocyanates, for example, aromatic, aliphatic, arylalkylenyl, cycloaliphatic diisocyanate, or a combination thereof. It should be understood that the thermoplastic polyurethane, and the diisocyanates from which it is derived, need not be the same as in the substrate polyurethane. Exemplary useful diisocyanates for making the thermoplastic polyurethane in the primer layer include hexamethylene 1,6-diisocyanate (HDI), 1,12-dodecane diisocyanate, isophorone diisocyanate, toluene diisocyanate, dicyclohexylmethane 4,4'diisocyanate, and diphenylmethane 4,4'-diisocyanate (MDI).

Typically, polyurethanes are made in the presence of a catalyst, for example, a tin II or tin IV salt (e.g., dibutyltin dilaurate, stannous octanoate, stannous oleate, tin dibutyldi-(2-ethyl hexanoate), tin (II) 2-ethyl hexanoate, and stannous chloride) or a tertiary amine (e.g., triethylamine, tributylamine, triethylenediamine, tripropylamine, bis(dimethylaminoethyl)ether, ethyl morpholine, 2,2'-dimorpholinodiethyl ether, 1,4-diazabicyclo[2.2.2]octane (DABCO), and 1,8-diazabicyclo[5.4.0.]undec-7-ene (DBU). In some embodiments, a tin salt is used. The amount of catalyst present will depend on the particular reaction. Generally, however, suitable catalyst concentrations are from about 0.001 percent to about 10 percent (in some embodiments, about 0.1 percent to about 5 percent or about 0.1 to about 1 percent) by weight based on the total weight of the reactants.

In embodiments wherein the thermoplastic polymer in the primer layer 24 is a thermoplastic polyester, the thermoplastic polyester can be made from a variety of difunctional carboxylic acids or equivalents thereof. For example, carboxylic acids having aryl, alkyl, arylalkylenyl, or cycloalkyl groups, or a combination thereof may be useful. Exemplary useful dicarboxylic acids for providing a thermoplastic polyester include: 2,6-naphthalenedicarboxylic acid; terephthalic acid; isophthalic acid; phthalic acid; azelaic acid; adipic acid; sebacic acid; norbornenedicarboxylic acid; bicyclooctanedicarboxylic acid; 1,6-cyclohexanedicarboxylic acid; t-butyl isophthalic acid, trimellitic acid, sodium sulfonated isophthalic acid; and 4,4'-biphenyldicarboxylic acid. Acid halides and lower alkyl (that is, $C_{1-4}$) esters of these acids, such as methyl or ethyl esters may also be used as functional equivalents.

The primer layer 24, which may include a poly(propylene oxide) homopolymer, a copolymer of poly(ethylene oxide) and poly(propylene oxide), or a thermoplastic including a poly(propylene oxide) segment or a segment including copolymerized poly(propylene oxide) and poly(ethylene oxide) as described in any of the above embodiments, may be applied to the substrate in a variety of ways. For example, the primer polymer may be may be solution cast by dissolving the polymer in a suitable solvent (e.g., tetrahydrofuran or ethyl acetate), coating the resulting solution onto the substrate 22, and drying to remove solvent. It is also possible that the primer may be cast into a film using a solventless process (e.g., melt casting). The primer layer 24 (in some embodiments, after drying) may have a thickness of 0.01 micrometers to 1.0 micrometers (in some embodiments, 50 nanometers to 100 nanometers). In some embodiments, the primer layer may be a discontinuous layer on the substrate, which may be deposited on the substrate, for example, by pattern coating.

Silicone adhesives 16, 26 useful for practicing the present disclosure may be silicone gel adhesives or silicone pressure sensitive adhesives. Some silicone pressure sensitive adhesive compositions useful for practicing the present disclosure are commercially available, for example, from Dow Corning, Midland, Mich., under the trade designation "7735" and from Momentive Performance Materials, Columbus, Ohio, under the trade designation "SILGRIP 6574". Suitable silicone adhesives for medical applications include lightly crosslinked silicone gel adhesives that are soft, tacky, elastic materials with moderate adhesive strength. Silicone gel adhesives typically have excellent wetting characteristics due to their inherent low glass transition temperature, low surface energy, and relatively low storage modulus. The inertness and lack of reactivity of the silicone materials make silicone gels suitable for gentle-to-skin adhesive applications. Additionally, the elastic nature of the crosslinked gel and lack of interaction with hair surfaces debond the adhesives from skin by stretch releasing and further reduces the instances of pain during removal. Some silicone adhesives (e.g., silicone gel adhesives) useful for practicing the present disclosure are commercially available, for example, from Dow Corning under the trade designation "MG 7-9850"; from Wacker Chemie AG, Munich, Germany, under the trade designation "SILPURAN 2130"; from Bluestar Silicones, East Brunswick, N.J., under the trade desig- nations "RT GEL 4317 and "SILBIONE RT GEL 4320"; and from NuSIL Silicone Technology, Carpinteria, Calif., under the trade designations "MED-6345" and "MED-6350".

In some embodiments, silicone adhesives useful for practicing the present disclosure are formed by an addition cure reaction between vinyl-terminated poly(dimethylsiloxane) (PDMS) and hydrogen terminated PDMS, in the presence of a hydrosilation catalyst (e.g., platinum complex). Vinyl-terminated and hydrogen terminated PDMS chains are referred to as 'functionalized' silicones due to their specific chemical moieties. Individually, such functional silicones are generally not reactive; however, together they form a reactive silicone system. Additionally, silicate resin tackifiers, such as those described in further detail below, and PDMS with multiple hydrogen functionalities (crosslinkers) can be formulated to modify the adhesive properties of the silicone adhesives. Silicone adhesives resulting from this addition reaction are typically called silicone gel adhesives if they are very lightly crosslinked polydimethysiloxane (PDMS) networks with some level of free (not crosslinked) PDMS fluid and no or low levels of tackifying resin. By contrast, silicone pressure sensitive adhesives are typically formulated with higher levels of tackifying resins (e.g., 45-60 weight percent). The amount of tackifying resin and control of crosslink density (the chain length of the polymer between the crosslinks) are features that are carefully controlled in silicone adhesives useful for medical articles that will adhere to skin. Silicone adhesives (e.g., silicone gel adhesives) useful for practicing the present disclosure may also include hydroxyl functional groups. Examples of such adhesives are disclosed in Int. Pat. App. Pub. No. WO 2005/102403 (Gantner et al.).

In some embodiments, the silicone adhesive is a radiation crosslinked silicone adhesive, such as those disclosed in U.S. Pat. App. Pub. No. 2011/0212325 (Determan et al.), the disclosure of which is herein incorporated by reference. Radiation crosslinking processes typically require less space and less capital equipment than catalyzed thermal curing processes. Also, radiation crosslinking is typically a faster process than thermal curing, which results in higher throughput and lower manufacturing costs. Radiation curing is typically accomplished through high energy radiation, such as electron beam or gamma ray radiation, as described in U.S. Pat. App. Pub. No. 2011/0212325 (Determan et al.). Reactive functional groups are not required in the adhesive compositions in order to make radiation crosslinked silicone adhesives.

Silicone adhesive compositions, which may be crosslinked to from silicone adhesives in some embodiments of the adhesives articles disclosed herein and the methods of making them, can include silicone oils, fluids, gums, elastomers, or resins. Generally, lower molecular weight, lower viscosity silicone materials are referred to as fluids or oils, while higher molecular weight, higher viscosity materials are referred to as gums; however, there is no sharp distinction between these terms. Silicone elastomers typically have crosslinking (e.g., polar blocks that associate via hydrogen bonding or phase separation) that provides the elasticity. As used herein, the terms "fluid" and "oil" refer to materials having a dynamic viscosity at 25° C. of no greater than 1,000,000 mPa·sec (e.g., less than 600,000 mPa·sec), while materials having a dynamic viscosity at 25° C. of greater than 1,000,000 mPa·sec (e.g., at least 10,000,000 mPa·sec) are referred to as "gums".

Useful adhesive compositions useful for making silicone adhesives in the articles and methods disclosed herein include poly diorganosiloxanes, i.e., materials comprising a polysiloxane backbone. In some embodiments, useful diorganosiloxanes can be described by the following formula illustrating a siloxane backbone with aliphatic and/or aromatic substituents:

wherein R1, R2, R3, and R4 are independently selected from the group consisting of an alkyl group and an aryl group, each R5 is an alkyl group and n and m are integers, and at least one of m or n is not zero. In some embodiments, one or more of the alkyl or aryl groups may contain a halogen substituent, e.g., fluorine. For example, in some embodiments, one or more of the alkyl groups may be —$CH_2CH_2C_4F_9$.

In some embodiments, R5 is a methyl group, i.e., the poly diorganosiloxane material is terminated by trimethylsiloxy groups. In some embodiments, R1 and R2 are alkyl groups and n is zero, i.e., the material is a poly(dialkylsiloxane). In some embodiments, the alkyl group is a methyl group, i.e., poly(dimethylsiloxane) ("PDMS"). In some embodiments, R1 is an alkyl group, R2 is an aryl group, and n is zero, i.e., the material is a poly(alkylarylsiloxane). In some embodiments, R1 is methyl group and R2 is a phenyl group, i.e., the material is poly(methylphenylsiloxane). In some embodiments, R1 and R2 are alkyl groups and R3 and R4 are aryl groups, i.e., the material is a poly(dialkyldiarylsiloxane). In some embodiments, R1 and R2 are methyl groups, and R3 and R4 are phenyl groups, i.e., the material is poly(dimethyldiphenylsiloxane).

In some embodiments, the poly diorganosiloxanes may be branched. For example, one or more of the R1, R2, R3, and/or R4 groups may be a linear or branched siloxane with alkyl or aryl (including halogenated alkyl or aryl) substituents and terminal R5 groups.

The poly diorganosiloxanes described above are considered "nonfunctional" since the R1, R2, R3, R4, and R5 groups are nonfunctional groups (e.g., alkyl or aryl groups consisting of carbon, hydrogen, and in some embodiments, halogen (e.g., fluorine) atoms).

In some embodiments, the polysiloxane useful for making silicone adhesives in the articles and methods disclosed herein may be a functional polysiloxane. Functional polysiloxanes include specific reactive groups attached to the polysiloxane backbone of the starting material (e.g., hydrogen, hydroxyl, vinyl, allyl, or acrylic groups). As used herein, a "functionalized poly diorganosiloxane material" is one in which at least one of the R-groups of Formula 2 is a functional group.

In some embodiments, a functional poly diorganosiloxane material is one is which at least 2 of the R-groups are functional groups. Generally, the R-groups of Formula 2 may be independently selected. In some embodiments, at least one functional group is selected from the group consisting of a hydride group, a hydroxy group, an alkoxy group, a vinyl group, an epoxy group, and an acrylate group. Typically, a functional polydiorgano siloxane will have a mixture of reactive groups and nonfunctional groups on the polysiloxane backbone. That is, in Formula 2, some of the R groups are reactive groups and others are nonfunctional groups. In some embodiments, the functionalized poly diorganosiloxane materials may be branched. For example, one or more of the R groups may be a linear or branched siloxane with functional and/or non-functional substituents.

In some embodiments, silicone adhesives useful in the articles and methods of the present disclosure may be prepared by combining one or more poly diorganosiloxane materials (e.g., silicone oils or fluids), optionally with an appropriate tackifying resin, coating the resulting adhesive composition on the substrate or primer, and crosslinking the adhesive composition to form the silicone adhesive. In some embodiments, coating the silicone adhesive composition includes pattern coating. Generally, any known additives useful in the formulation of adhesives may also be included.

If included, generally, any known tackifying resin may be used, e.g., in some embodiments, silicate tackifying resins may be used. In some exemplary adhesive compositions, a plurality of silicate tackifying resins can be used to achieve desired performance.

Suitable silicate tackifying resins include those resins composed of the following structural units M (i.e., monovalent $R'_3SiO_{1/2}$ units), D (i.e., divalent $R'_2SiO_{2/2}$ units), T (i.e., trivalent $R'SiO_{3/2}$ units), and Q (i.e., quaternary $SiO_{4/2}$ units), and combinations thereof. Typical exemplary silicate resins include MQ silicate tackifying resins, MQD silicate tackifying resins, and MQT silicate tackifying resins. These silicate tackifying resins usually have a number average molecular weight in the range of 100 to 50,000-gm/mole, e.g., 500 to 15,000 gm/mole and generally R' groups are methyl groups.

MQ silicate tackifying resins are copolymeric resins where each M unit is bonded to a Q unit, and each Q unit is bonded to at least one other Q unit. Some of the Q units are bonded to only other Q units. However, some Q units are bonded to hydroxyl radicals resulting in $HOSiO_{3/2}$ units (i.e., "$T^{OH}$" units), thereby accounting for some silicon-bonded hydroxyl content of the silicate tackifying resin.

Such resins are described in, for example, *Encyclopedia of Polymer Science and Engineering*, vol. 15, John Wiley & Sons, New York, (1989), pp. 265-270, and U.S. Pat. No. 2,676,182 (Daudt et al.), U.S. Pat. No. 3,627,851 (Brady), U.S. Pat. No. 3,772,247 (Flannigan), and U.S. Pat. No. 5,248,739 (Schmidt et al.). Other examples are disclosed in U.S. Pat. No. 5,082,706 (Tangney). The above-described resins are generally prepared in solvent. Dried or solventless, M silicone tackifying resins can be prepared, as described in U.S. Pat. No. 5,319,040 (Wengrovius et al.), U.S. Pat. No. 5,302,685 (Tsumura et al.), and U.S. Pat. No. 4,935,484 (Wolfgruber et al.). Certain MQ silicate tackifying resins can be prepared by the silica hydrosol capping process described in U.S. Pat. No. 2,676,182 (Daudt et al.) as modified according to U.S. Pat. No. 3,627,851 (Brady), and U.S. Pat. No. 3,772,247 (Flannigan).

The level of silicon bonded hydroxyl groups (i.e., silanol) on the MQ resin may be reduced to no greater than 1.5 weight percent, no greater than 1.2 weight percent, no greater than 1.0 weight percent, or no greater than 0.8 weight percent based on the weight of the silicate tackifying resin. This may be accomplished, for example, by reacting hexamethyldisilazane with the silicate tackifying resin. Such a reaction may be catalyzed, for example, with trifluoroacetic acid. Alternatively, trimethylchlorosilane or trimethylsilylacetamide may be reacted with the silicate tackifying resin, a catalyst not being necessary in this case.

MQD silicone tackifying resins are terpolymers having M, Q and D units. In some embodiments, some of the methyl R' groups of the D units can be replaced with vinyl ($CH_2=CH-$) groups ("$D^{Vi}$" units). MQD silicone tackifying resins are terpolymers having $R_3SiO_{1/2}$ units ("M" units), $SiO_{4/2}$ units ("Q" units), and $R_2SiO_{2/2}$ units ("D" units) such as are taught in U.S. Pat. No. 2,736,721 (Dexter). MQT silicate tackifying resins are terpolymers having M, Q and T units. MQT silicate tackifying resins are terpolymers having $R_3SiO_{1/2}$ units, $SiO_{4/2}$ units and $RSiO_{3/2}$ units ("T" units) such as are taught in U.S. Pat. No. 5,110,890 (Butler) and Japanese Kokai HE 2-36234.

Suitable silicate tackifying resins are commercially available from sources such as Dow Corning (e.g., under the trade designation "DC 2-7066"), Momentive Performance Materials (e.g., under the trade designations "SR545" and "SR1000"), and Wacker Chemie AG (e.g., under the trade designation "BELSIL TMS-803").

The polysiloxane material, the tackifying resin, if present, and any optional additives (e.g., fillers, pigments, additives for improving adhesion, pharmaceutical agents, cosmetic agents, natural extracts, silicone waxes, and rheology modifiers) may be combined by any of a wide variety of known means prior to being coated and cured. For example, in some embodiments, the various components may be pre-blended using common equipment such as mixers, blenders, mills, and extruders.

In some embodiments, the materials may be dissolved in a solvent, coated, and dried prior to curing. In some embodiments, solventless compounding and coating processes may be used. In some embodiments, solventless coating may occur at about room temperature. For example, in some embodiments, the materials may have kinematic viscosity of no greater than 100,000 centistokes (cSt), e.g., no greater than 50,000 cSt. However, in some embodiments, hot melt coating processes such as extrusion may be used, e.g., to reduce the viscosity of higher molecular weight materials to values more suitable for coating. The various components may be added together, in various combinations or individually, through one or more separate ports of an extruder, blended (e.g., melt mixed) within the extruder, and extruded to form the hot melt coated composition.

In some embodiments of the method of making an adhesive article according to the present disclosure, crosslinking the silicone adhesive composition includes exposing the adhesive composition to radiation to form a radiation crosslinked silicone adhesive. Likewise, in some embodiments of the adhesive article according to the present disclosure, the silicone adhesive is a radiation crosslinked silicone adhesive. In some embodiments, the silicone adhesive may be crosslinked through exposure to E-beam irradiation. In some embodiments, the silicone adhesive may be crosslinked through exposure to gamma irradiation. In some embodiments, a combination of electron beam curing and gamma ray curing may be used. For example, in some embodiments, the silicone adhesive may be partially crosslinked by exposure to electron beam irradiation. Subsequently, the silicone adhesive may be further crosslinked by gamma irradiation.

A variety of procedures for E-beam and gamma ray curing may be useful. The crosslinking depends on the specific equipment used, and those skilled in the art can define a dose calibration model for the specific equipment, geometry, and line speed, as well as other process parameters.

Commercially available electron beam generating equipment is readily available. Generally, a support film (e.g., polyester terephthalate support film) runs through a chamber, and the substrates, in some embodiments, with the primers, with the adhesive compositions coated thereon are attached to the support film. Generally, the chamber is inerted (e.g., the oxygen-containing room air is replaced with an inert gas, e.g., nitrogen) while the samples are e-beam crosslinked, particularly when open-face curing (e.g., in the absence of a release liner on top of the adhesive). Single or multiple passes through the chamber may be useful.

Commercially available gamma irradiation equipment includes equipment often used for gamma irradiation sterilization of products for medical applications. In some embodiments, such equipment may be used to crosslink, or partially crosslink the adhesive compositions disclosed herein. In some embodiments, such curing may occur simultaneously with a sterilization process for a semi-finished or finished product, for example a tape or wound dressing.

The thickness of the silicone adhesive in the adhesive articles according to the present disclosure is not particularly limited. In some embodiments, the thickness will be at least 10 microns, and in some embodiments, at least 20 microns. In some embodiments, the thickness will be no greater than 400 microns, and in some embodiments, no greater than 200 microns.

In some embodiments, the adhesive article is suitable for application to skin. Therefore, the adhesive article 10 or 20 can be a medical tape, bandage, or wound dressing. In some embodiments, the adhesive article can be an IV site dressings, a buccal patch, or a transdermal patch. In some embodiments, the adhesive articles according to the present disclosure may be adhered to the skin of humans and/or animals. The adhesive articles according to the present disclosure may include other materials such as polymeric materials, plastics, natural macromolecular materials (e.g., collagen, wood, cork, and leather), paper, films, foams, woven cloth and non-woven cloth, and combinations of these materials.

As the Examples below demonstrate, the addition of poly(propylene oxide), copolymers of poly(ethylene oxide) and poly(propylene oxide), or thermoplastic polyurethanes including segments of such (co)polymers disclosed herein in a substrate or backing of an adhesive article or as a primer on the substrate increases the strength of the bond between a silicone adhesive and a substrate. The adhesive strength between the silicone adhesive and the substrate is increased such that it either exceeds the cohesive strength of the silicone adhesive or the adhesive strength between the silicone adhesive and the testing tape (3M™ Polyester Tape 8403).

Typically, useful primers can contain reactive functional groups (e.g., epoxy, acrylic, isocyanate, vinyl, or hydrolysable silanes) to form covalent bonds with a substrate and/or an adhesive coated onto the substrate. Also, primers can contain acidic or basic groups that compliment those in the substrate or adhesive to improve adhesion. Still other methods for improving adhesion between an adhesive and a substrate include plasma treatment, corona treatment, or flame treatment of a substrate surface to clean or roughen the surface and/or provide polar functional groups on the surface. In contrast, in the adhesive articles according to and/or made according to the present disclosure, the adhesive strength between the substrate and the adhesive is improved even though the poly(propylene oxide) polymers, copolymers, or polyurethanes or polyesters containing these do not contain reactive functional groups, acids, or bases to promote interaction with the substrate or the adhesive. An extra step of plasma, corona, or flame treatment of the substrate surface is not required for the adhesive articles disclosed herein.

Furthermore, as shown in the examples below, not all poly(propylene oxide) polymers or copolymers of poly(ethylene oxide) and poly(propylene oxide) improve the adhesive strength between the substrate and the adhesive. As described above, when the weight ratio of poly(ethylene oxide) to poly(propylene oxide) exceeds 3:1, or 2:1 at molecular weights of higher than 10,000 grams per mole, the adhesion between the substrate and the silicone adhesive may be diminished.

Some Embodiments of the Disclosure

In a first embodiment, the present disclosure provides an adhesive article comprising:

a substrate comprising a polymer blend, the polymer blend comprising:

a polymer having a number average molecular weight of at least 1000 grams per mole, wherein the polymer is a poly(propylene oxide) or a copolymer of poly(ethylene oxide) and poly(propylene oxide), and at least one of a thermoplastic polyurethane or a thermoplastic polyester; and a silicone adhesive disposed on the substrate, wherein the copolymer has a weight ratio of poly(ethylene oxide) to poly(propylene oxide) of up to 3:1, with the proviso that if the copolymer has a number average molecular weight of at least 10,000 grams per mole, the weight ratio of poly(ethylene oxide) to poly(propylene oxide) is up to 2:1.

In a second embodiment, the present disclosure provides the adhesive article of the first embodiment, wherein the polymer blend comprises up to fifteen percent by weight of the polymer having a number average molecular weight of at least 1000, based on the total weight of the polymer blend. In any of these embodiments, the polymer blend may comprise at least three percent by weight of the polymer having a number average molecular weight of at least 1000, based on the total weight of the polymer blend.

In a third embodiment, the present disclosure provides the adhesive article of the first or second embodiment, wherein the weight ratio of poly(ethylene oxide) to poly(propylene oxide) in the copolymer is up to 1:1.

In a fourth embodiment, the present disclosure provides the adhesive article of any one of the first to third embodiments, wherein the polymer is a hydroxyl-terminated, triblock copolymer of poly(ethylene oxide) and poly(propylene oxide).

In a fifth embodiment, the present disclosure provides an adhesive article comprising:

a substrate comprising at least one of a thermoplastic polyurethane or a polyester;

a primer layer disposed on the substrate, the primer layer comprising a polymer, wherein the polymer is a poly(propylene oxide) having a number average molecular weight of at least 1000 grams per mole, a copolymer of poly(ethylene oxide) and poly(propylene oxide) having a number average molecular weight of at least 1000 grams per mole, or a thermoplastic polymer comprising poly(propylene oxide)

segments or copolymerized poly(ethylene oxide) and poly(propylene oxide) segments; and a silicone adhesive disposed on the primer layer,
wherein in the copolymer of poly(ethylene oxide) and poly(propylene oxide), the weight ratio of poly(ethylene oxide) to poly(propylene oxide) is up to 3:1, with the proviso that if the copolymer has a number average molecular weight of at least 10,000 grams per mole, the weight ratio of poly(ethylene oxide) to poly(propylene oxide) is up to 2:1.

In a sixth embodiment, the present disclosure provides the adhesive article of the fifth embodiment, wherein the thermoplastic polymer in the primer layer is a thermoplastic polyurethane or thermoplastic polyester comprising poly(propylene oxide) segments or a thermoplastic polyurethane or thermoplastic polyester comprising segments of copolymerized poly(ethylene oxide) and poly(propylene oxide) with a weight ratio of poly(ethylene oxide) to poly(propylene oxide) of up to 3:1, with the proviso that if the segments of copolymerized poly(ethylene oxide) and poly(propylene oxide) have a number average molecular weight of at least 10,000 grams per mole, the weight ratio of poly(ethylene oxide) to poly(propylene oxide) is up to 2:1.

In a seventh embodiment, the present disclosure provides the adhesive article of the sixth embodiment, wherein in the segments of copolymerized poly(ethylene oxide) and poly(propylene oxide), the weight ratio of poly(ethylene oxide) to poly(propylene oxide) is up to 1:1.

In an eighth embodiment, the present disclosure provides the adhesive article of the fifth embodiments, wherein the polymer in the primer layer is a poly(propylene oxide) or a copolymer of only poly(ethylene oxide) and poly(propylene oxide).

In a ninth embodiment, the present disclosure provides the adhesive article of the eighth embodiment, wherein the weight ratio of poly(ethylene oxide) to poly(propylene oxide) in the copolymer is up to 1:1.

In a tenth embodiment, the present disclosure provides the adhesive article of the eighth or ninth embodiment, wherein the polymer in the primer layer is a hydroxyl-terminated, tri-block copolymer of poly(ethylene oxide) and poly(propylene oxide).

In an eleventh embodiment, the present disclosure provides the adhesive article of any one of the first to tenth embodiments, wherein the polymer has a number average molecular weight of up to 20,000 grams per mole.

In a twelfth embodiment, the present disclosure provides the adhesive article of the eleventh embodiment, wherein the polymer has a number average molecular weight of up to 5000 grams per mole.

In a thirteenth embodiment, the present disclosure provides the adhesive article of any of the first to twelfth embodiments, wherein the silicone adhesive is a radiation crosslinked silicone adhesive.

In a fourteenth embodiment, the present disclosure provides the adhesive article of any of the first to thirteenth embodiments, wherein the silicone adhesive comprises a crosslinked poly(diorganosiloxane).

In a fifteenth embodiment, the present disclosure provides the adhesive article of the fourteenth embodiment, wherein the crosslinked poly(diorganosiloxane) comprises silanol, alkyl, or aryl terminal groups or a combination thereof, and wherein alkyl and aryl are optionally halogenated.

In a sixteenth embodiment, the present disclosure provides the adhesive article of any of the first to fifteenth embodiments, wherein the silicone adhesive comprises a silicate resin tackifier.

In a seventeenth embodiment, the present disclosure provides the adhesive article of any of the first to sixteenth embodiments, wherein the substrate includes a polyester- or polyether-based thermoplastic polyurethane.

In an eighteenth embodiment, the present disclosure provides the adhesive article of any of the first to seventeenth embodiments, wherein the adhesive article is a bandage, tape, or wound dressing.

In a nineteenth embodiment, the present disclosure provides a method of making an adhesive article of any one of the first to fourth embodiments or any one of eleventh to eighteenth embodiments as they depend on any one of the first to fourth embodiments, the method comprising:

providing the substrate;
coating a silicone adhesive composition onto the substrate; and
crosslinking the silicone adhesive composition to form the silicone adhesive.

In a twentieth embodiment, the present disclosure provides the method of the nineteenth embodiment, wherein the polymer blend is solution coated onto a film to form the substrate.

In a twenty-first embodiment, the present disclosure provides a method of making the adhesive article of any one of the fifth to tenth embodiments or any one of the eleventh to eighteenth embodiments as dependent on any one of the fifth to tenth embodiments, the method comprising:

coating the primer layer onto the substrate;
coating a silicone adhesive composition onto the primer layer; and
crosslinking the silicone adhesive composition to form the silicone adhesive.

In a twenty-second embodiment, the present disclosure provides the method of the twenty-first embodiment, wherein coating the primer layer onto the substrate comprises pattern-coating.

In a twenty-third embodiment, the present disclosure provides the method of the twenty-first or twenty-second embodiment, wherein the primer layer improves the adhesion between the substrate and the silicone adhesive.

In a twenty-fourth embodiment, the present disclosure provides the method of any one of the nineteenth to twenty-third embodiments, wherein coating the silicone adhesive composition comprises pattern-coating.

In a twenty-fifth embodiment, the present disclosure provides the method of any one of the nineteenth to twenty-fourth embodiments, wherein crosslinking the silicone adhesive composition comprises exposing the silicone adhesive composition to radiation to form a radiation-crosslinked silicone adhesive.

In a twenty-sixth embodiment, the present disclosure provides the method of the twenty-fifth embodiment, wherein the radiation comprises at least one of electron-beam or gamma radiation.

In a twenty-seventh embodiment, the present disclosure provides method of improving adhesion of a silicone adhesive to a substrate comprising a thermoplastic polyurethane or thermoplastic polyester, the method comprising blending a polymer with the thermoplastic polyurethane or thermoplastic polyester to form the substrate, wherein the a polymer has a number average molecular weight of at least 1000 grams per mole, wherein the polymer is a poly(propylene oxide) or a copolymer of poly(ethylene oxide) and poly(propylene oxide) having a weight ratio of poly(ethylene oxide) to poly(propylene oxide) of up to 3:1, with the proviso that if the copolymer has a number average molecular weight of at least 10,000 grams per mole, the weight ratio of poly(ethylene oxide) to poly(propylene oxide) is up to 2:1.

EXAMPLES

The present disclosure is further illustrated by the following examples, but the particular materials and amounts thereof recited in these examples, as well as other conditions and details, should not be construed to unduly limit this invention.

Materials

Materials utilized in the following Examples are shown in Table 1.

TABLE 1

Materials

| Component | Source | Description |
|---|---|---|
| "PLURONIC ™ F127" | BASF, Florham Park, NJ | Triblock copolymer with an Mn approximately 13000 g/mol and PEO to PPO ratio of 70/30 |
| "PLURONIC ™ P65" | BASF, Florham Park, NJ | Triblock copolymer with an Mn approximately 4000 g/mol and a PEO to PPO ratio of 50/50 |
| "PLURONIC ™ F68" | BASF, Florham Park, NJ | Triblock copolymer with an Mn approximately 9850 g/mol and PEO to PPO ratio of 80/20 |
| "PLURONIC ™ F108" | BASF, Florham Park, NJ | Triblock copolymer with an Mn approximately 16700 g/mol and a PEO to PPO ratio of 80/20 |
| "PLURONIC ™ P85" | BASF, Florham Park, NJ | Triblock copolymer with an Mn approximately 5300 g/mol and PEO to PPO ratio of 50/50 |
| "PLURONIC ™ L101" | BASF, Florham Park, NJ | Triblock copolymer with an Mn approximately 3700 g/mol and a PEO to PPO ratio of 10/90 |
| "PLURONIC ™ L61" | BASF, Florham Park, NJ | Triblock copolymer with an Mn approximately 2200 g/mol and PEO to PPO ratio of 10/90 |
| "PLURONIC ™ L103" | BASF, Florham Park, NJ | Triblock copolymer with an Mn approximately 4800 g/mol and a PEO to PPO ratio of 30/70 |
| "PLURONIC ™ L121" | BASF, Florham Park, NJ | Triblock copolymer with an Mn approximately 4500 g/mol and PEO to PPO ratio of 10/90 |
| "PLURONIC ™ F87" | BASF, Florham Park, NJ | Triblock copolymer with an Mn approximately 8800 g/mol and a PEO to PPO ratio of 70/30 |
| "PLURONIC ™ P105" | BASF, Florham Park, NJ | Triblock copolymer with an Mn approximately 6700 g/mol and a PEO to PPO ratio of 50/50 |
| PPO-ran-PEO | Sigma-Aldrich, St. Louis, MO | Poly(ethylene glycol)-random-poly(propylene glycol), Mn 12000 g/mol |
| PPO 2500 | Sigma-Aldrich, St. Louis, MO | Poly(propylene glycol) monobutyl ether homopolymer with a molecular weight of 2500 g/mol |
| PPO 425 | PPG industries, Gurnee, IL | Polypropylene oxide homopolymer with a molecular weight of 425 g/mol |
| "ESTANE ™ 58237" | Lubrizol, Wickliffe, OH | Aromatic polyether-based thermoplastic polyurethane, Shore hardness of 90A |
| "ESTANE ™ 58309" | Lubrizol, Wickliffe, OH | Aromatic polyether-based thermoplastic polyurethane, Shore hardness of 85A |
| "ESTANE ™ 58213" | Lubrizol, Wickliffe, OH | Aromatic polyester-based thermoplastic polyurethane, Shore hardness of 75A |
| "IROGRAN ™ A 60 E 4902" | Huntsman, The Woodlands, TX | Polyester based thermoplastic polyurethane, Shore hardness of 55A |
| "XIAMETER ™ OHX-4070" | Dow Corning, Midland, MI | Silicone fluid, 50,000 cSt viscosity |
| "MQ803TF" | Wacker Chemical Corp., Adrian, MI | Co-hydrolysis product of tetraalkoxy silane (Q unit) and trimethyl-ethoxy silane (M unit) |
| H12MDI | Bayer Materials Science, Pittsburgh, PA | dicyclohexylmethane diisocyanate |
| DBU | Sigma-Aldrich | 1,8-diazabicyclo[5.4.0]undec-7-ene |

Preparative Example 1

Preparation of polyurethane for Example E-20: "PLURONIC™ L61" copolymer (28 grams) was dissolved in ethyl acetate and heated to 50° C. To this mixture was added 4 grams of H12MDI. DBU catalyst (0.06 grams) was added, and the mixture was heated to 80° C. The mixture was allowed to react overnight or until all of the OH was consumed. The isocyanate terminated prepolymer was then treated with methanol (1 gram) and stirred until all of the isocyanate had been consumed (as measured by IR spectroscopy). The percent solids of the solution were then measured, and the solution was diluted to 5% solids to produce the coating solution.

Preparative Example 2

Preparation of polyurethane for Example E-21: "PLURONIC™ L101" copolymer (20 grams) was dissolved in ethyl acetate and heated to 50° C. To this mixture was added 1.5 grams H12MDI. DBU catalyst (0.04 grams) was added and the mixture was heated to 80° C. The mixture was allowed to react overnight or until all of the OH was consumed. The isocyanate terminated prepolymer was then treated with methanol (1 gram) and stirred until all of the isocyanate had been consumed (as measured by IR spectroscopy). The percent solids of the solution were then measured, and the solution was diluted to 5% solids to produce the coating solution.

Appearance

A 2-4 inch section of 3M™ Polyester Tape "8403" was laminated to the adhesive side of a sample tape. The "8403"

tape was applied with 2 passes of a 2 kg roller at 30.5 cm/min and allowed to dwell for 5-30 minutes. The "8403" tape was removed at 30.5 cm/min at 180 degrees. After peeling the tape from the sample adhesive, the backing was inspected for adhesive residue. A "fail" indicates the adhesive was cleanly removed from the backing, with no adhesive residue left on the backing. A "pass" indicates the adhesive cohesively split, leaving residue on the backing and on the "8403" tape. Pass indicates the bond strength between the adhesive and the backing is greater than the cohesive strength of the adhesive.

Example 1 (E-1)

Backing

The backing was prepared by dissolving 19 wt % "ESTANE™ 58309" polyurethane and 1 wt % PPO 2500 additive in 80 wt % tetrahydrofuran (20% total solids). The additive concentration was 5% on a solids basis. This solution was cast on a polyethylene terephthalate film (PET) with a knife coater and dried at 70° C. for 10 minutes. The resulting backing after drying was approximately 0.05 mm thick. The backing was not removed from the PET film before coating with adhesive as described below.

Adhesive

The adhesive was prepared by blending "OHX-4070" and "MQ803TF" in the weight ratio of 69/31. The adhesive was coated on the backing using conventional coating methods and further crosslinked with e-beam irradiation to form a tacky film. The radiation processing was performed on a Model 40767 electron beam generating apparatus (PCT, Davenport, Iowa). A support film (PET) was run through the inerted chamber of the apparatus. The adhesives coated on the backings were attached to the support film and conveyed at a fixed speed of about 9 meters/min through the e-beam apparatus. The adhesive and process is described in U.S. Pat. App. Pub. No. 2011/0212325 (Determan et al.). This adhesive was utilized in all Examples and Comparatives.

Example 2 Through Example 6 (E-2 to E-6)

Examples 2 through 6 were prepared as described in Example 1, with the polyurethanes and additives shown in Table 2.

Example 7 (E-7)

Primer Layer on Backing

The backing was prepared by melt casting "ESTANE™ 58213" polyurethane into a 0.05 mm film. Ethyl acetate (95 wt %) and "PLURONIC™ L101" copolymer (5 wt %) were combined in a jar and allowed to dissolve. This solution was coated onto the "ESTANE™ 58213" polyurethane film using a #10 Meyer rod and dried at 70° C. for 10 minutes to form a primer layer. The adhesive was prepared as in Example 1.

Examples 8 Through 19 (E-8 Through E-19)

The backings and primers were prepared as in Example 7, with the materials shown in Table 3. The adhesive was prepared as in E-1.

Example 20 (E-20)

A backing made from "ESTANE™ 58309" polyurethane according to the method described in Example 7 was primed with the polyurethane prepared in Preparative Example 1 according to the method described in Example 7. The adhesive was prepared as in Example 1.

Example 21 (E-21)

A backing made from "ESTANE™ 58309" polyurethane according to the method described in Example 7 was primed with the polyurethane prepared in Preparative Example 2 according to the method described in Example 7. The adhesive was prepared as in Example 1.

Example 22

A backing made from "ESTANE™ 58213" polyurethane according to the method described in Example 7 (with no primer layer) was coated with adhesive as in Example 1. To this adhesive coating a film of "ESTANE™ 58309" polyurethane primed with "PLURONIC™ P65" copolymer, as described in Example 7, was laminated to the film and allowed to dwell 48 hours prior to testing. Upon removal of the "ESTANE™ 58213" film the adhesive wholly transferred to the primed "ESTANE™ 58309" film. The resulting adhesive article was then tested according to the "Appearance" test method described above and found to pass.

Example 23

Example 23 was carried out as described in Example 22 with the modification that "PLURONIC™ L61" copolymer was used instead of "PLURONIC™ P65" copolymer. The resulting adhesive article was then tested according to the "Appearance" test method described above and found to pass.

Comparative Examples 1 Through 3 (C-1 Through C-3)

Comparative Examples 1 to 3 were prepared as described in Example 1, with the exception that no additive was used. The polyurethanes used are shown in Table 2.

Illustrative Examples 1 Through 8 (I-1 Through I-8)

Illustrative Examples 1 through 8 were prepared as described in Example 1, with the polyurethanes and additives shown in Table 2.

Comparative Examples 4 and 5 (C-4 and C-5)

The backings and adhesive were prepared as in Example 7, with the exception that no primer layer was utilized. The polyurethanes used for the backing are shown in Table 3.

Illustrative Examples 9 and 10 (I-9 and I-10)

Illustrative Examples 9 and 10 were prepared as in Example 7, using the materials shown in Table 3 for the backing and the primer layer.

Results

The materials used and the Appearance Test Method Results for the Examples, Illustrative Examples, and Comparative Examples are shown in Table 2, and Table 3. The percent additive is based on the % solids in the coating solution.

TABLE 2

Backings Containing Additives

| Sample | Backing | Additive | Additive (wt. %) | Appearance |
|---|---|---|---|---|
| E-1 | "ESTANE ™ 58309" | PPO 2500 | 5 | Pass |
| E-2 | "ESTANE ™ 58309" | "PLURONIC ™ P65" | 5 | Pass |
| E-3 | "IROGRAN ™ A60 E4902" | "PLURONIC ™ P65" | 5 | Pass |
| E-4 | "ESTANE ™ 58237" | "PLURONIC ™ P65" | 10 | Pass |
| E-5 | "ESTANE ™ 58237" | "PLURONIC ™ P65" | 5 | Pass |
| E-6 | "ESTANE ™ 58309" | PEO-ran-PPO | 5 | Pass |
| C-1 | "ESTANE ™ 58237" | none | none | Fail |
| C-2 | "ESTANE ™ 58309" | none | none | Fail |
| C-3 | "IROGRAN ™ A60 E4902" | none | none | Fail |
| I-1 | "ESTANE ™ 58237" | "PLURONIC ™ F127" | 5 | Fail |
| I-2 | "ESTANE ™ 58309" | "PLURONIC ™ F127" | 5 | Fail |
| I-3 | "ESTANE ™ 58237" | PPO 425 | 5 | Fail |
| I-4 | "ESTANE ™ 58309" | PPO 425 | 5 | Fail |
| I-5 | "IROGRAN ™ A60 E4902" | "PLURONIC ™ F127" | 5 | Fail |
| I-6 | "ESTANE ™ 58237" | "PLURONIC ™ P65" | 2.5 | Fail |
| I-7 | "ESTANE ™ 58237" | "PLURONIC ™ P65" | 1 | Fail |
| I-8 | "ESTANE ™ 58237" | "PLURONIC ™ P65" | 0.5 | Fail |

TABLE 3

Backings With Primers

| Sample | Backing | Primer | Appearance |
|---|---|---|---|
| E-7 | "ESTANE ™ 58213" | "PLURONIC ™ L101" | Pass |
| E-8 | "ESTANE ™ 58213" | "PLURONIC ™ P65" | Pass |
| E-9 | "ESTANE ™ 58213" | "PLURONIC ™ L61" | Pass |
| E-10 | "ESTANE ™ 58213" | "PLURONIC ™ P103" | Pass |
| E-11 | "ESTANE ™ 58213" | "PLURONIC ™ L121" | Pass |
| E-12 | "ESTANE ™ 58213" | "PLURONIC ™ F87" | Pass |
| E-13 | "ESTANE ™ 58213" | "PLURONIC ™ L105" | Pass |
| E-14 | "ESTANE ™ 58213" | "PLURONIC ™ P85" | Pass |
| E-15 | "ESTANE ™ 58309" | "PLURONIC ™ L61" | Pass |
| E-16 | "ESTANE ™ 58309" | "PLURONIC ™ P65" | Pass |
| E-17 | "ESTANE ™ 58309" | "PLURONIC ™ P103" | Pass |
| E-18 | "ESTANE ™ 58309" | "PLURONIC ™ L121" | Pass |
| E-19 | "ESTANE ™ 58309" | PPO 2500 | Pass |
| E-20 | "ESTANE ™ 58309" | Preparative Example 1 | Pass |
| E-21 | "ESTANE ™ 58309" | Preparative Example 2 | Pass |
| C-4 | "ESTANE ™ 58309" | — | Fail |
| C-5 | "ESTANE ™ 58213" | — | Fail |
| I-9 | "ESTANE ™ 58213" | "PLURONIC ™ F68" | Fail |
| I-10 | "ESTANE ™ 58213" | "PLURONIC ™ 108" | Fail |

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein.

What is claimed is:

1. An adhesive article comprising:
    a substrate comprising at least one of a thermoplastic polyurethane or a polyester;
    a primer layer disposed on the substrate, the primer layer comprising a polymer; and
    a silicone adhesive disposed on the primer layer,
wherein the polymer is a copolymer of poly(ethylene oxide) and poly(propylene oxide) having a number average molecular weight of at least 10,000 grams per mole and a weight ratio of poly(ethylene oxide) to poly(propylene oxide) of up to 2:1 or a thermoplastic polyurethane or thermoplastic polyester comprising copolymerized poly(ethylene oxide) and poly(propylene oxide) segments,
wherein the copolymerized poly(ethylene oxide) and poly(propylene oxide) segments have a number average molecular weight of at least 10,000 grams per mole and a weight ratio of poly(ethylene oxide) to poly(propylene oxide) of up to 2:1.

2. The adhesive article of claim 1, wherein the polymer in the primer layer is the thermoplastic polyurethane or thermoplastic polyester comprising copolymerized poly(ethylene oxide) and poly(propylene oxide) segments, wherein the copolymerized poly(ethylene oxide) and poly(propylene oxide) segments have a number average molecular weight of at least 10,000 grams per mole.

3. The adhesive article of claim 1, wherein the polymer in the primer layer is a copolymer of only poly(ethylene oxide) and poly(propylene oxide).

4. The adhesive article of claim 3, wherein the weight ratio of poly(ethylene oxide) to poly(propylene oxide) in the copolymer is up to 1:1.

5. The adhesive article of claim 3, wherein the polymer in the primer layer is a hydroxyl-terminated, tri-block copolymer of poly(ethylene oxide) and poly(propylene oxide).

6. The adhesive article of claim 1, wherein the silicone adhesive is a radiation crosslinked silicone adhesive.

7. The adhesive article of claim 1, wherein the silicone adhesive comprises a crosslinked poly(diorganosiloxane).

8. The adhesive article of claim 1, wherein the substrate includes a polyester- or polyether-based thermoplastic polyurethane.

9. The adhesive article of claim 1, wherein the adhesive article is a bandage, tape, or wound dressing.

10. A method of making the adhesive article of claim 1, the method comprising:
    coating the primer layer onto the substrate;
    coating a silicone adhesive composition onto the primer layer; and crosslinking the silicone adhesive composition to form the silicone adhesive.

11. The method of claim 10, wherein crosslinking the silicone adhesive composition comprises exposing the silicone adhesive composition to radiation to form a radiation-crosslinked silicone adhesive.

12. An adhesive article comprising:
a substrate comprising at least one of a thermoplastic polyurethane or a polyester;
a primer layer disposed on the substrate, the primer layer comprising a copolymer of only poly(ethylene oxide) and poly(propylene oxide) having a number average molecular weight of at least 1000 grams per mole; and
a silicone adhesive disposed on the primer layer,
wherein in the copolymer of only poly(ethylene oxide) and poly(propylene oxide), the weight ratio of poly(ethylene oxide) to poly(propylene oxide) is up to 3:1, with the proviso that if the copolymer has a number average molecular weight of at least 10,000 grams per mole, the weight ratio of poly(ethylene oxide) to poly(propylene oxide) is up to 2:1.

13. The adhesive article of claim 12, wherein the weight ratio of poly(ethylene oxide) to poly(propylene oxide) in the copolymer is up to 1:1.

14. The adhesive article of claim 12, wherein the polymer in the primer layer is a hydroxyl-terminated, tri-block copolymer of poly(ethylene oxide) and poly(propylene oxide).

15. The adhesive article of claim 12, wherein the silicone adhesive is a radiation crosslinked silicone adhesive.

16. The adhesive article of claim 12, wherein the silicone adhesive comprises a crosslinked poly(diorganosiloxane).

17. The adhesive article of claim 12, wherein the substrate includes a polyester- or polyether-based thermoplastic polyurethane.

18. The adhesive article of claim 12, wherein the adhesive article is a bandage, tape, or wound dressing.

19. A method of making the adhesive article of claim 12, the method comprising:
coating the primer layer onto the substrate;
coating a silicone adhesive composition onto the primer layer; and
crosslinking the silicone adhesive composition to form the silicone adhesive.

20. The method of claim 19, wherein crosslinking the silicone adhesive composition comprises exposing the silicone adhesive composition to radiation to form a radiation-crosslinked silicone adhesive.

* * * * *